US00PP11808P2

(12) United States Plant Patent
Heil

(10) Patent No.: US PP11,808 P2
(45) Date of Patent: Mar. 13, 2001

(54) CARNATION PLANT NAMED 'KOWIPA'

(75) Inventor: Jacob Johannes Heil, GS Aalsmeer (NL)

(73) Assignee: P. Kooij + Zonen B.V., Aalsmeer (NL)

( * ) Notice: Under 35 U.S.C. 154(b), the term of this patent shall be extended for 0 days.

(21) Appl. No.: 09/379,267

(22) Filed: Aug. 23, 1999

(51) Int. Cl.[7] ..... A01H 5/00

(52) U.S. Cl. ..... Plt./273

(58) Field of Search ..... Plt./273, 276, 277, Plt./281, 282, 272

(56) References Cited

PUBLICATIONS

GIITM UPOVROM Citation for 'Kowipa' as per QZ PBR981002; Jul. 20, 1998.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Carnation plant named 'Kowipa', characterized by its large purple and pink bi-colored flowers; compact, upright and mounded plant habit; good basal branching with about 10 lateral branches developing after pinching; dark green leaves; rapid growth rate; fragrant flowers; and good postproduction longevity.

1 Drawing Sheet

BACKGROUND OF THE INVENTION

The present invention relates to a new and distinct cultivar of Carnation plant, botanically known as *Dianthus caryophyllus,* and hereinafter referred to by the cultivar name 'Kowipa'.

The new Carnation is a product of a planned breeding program conducted by the Inventor in Aalsmeer, The Netherlands. The objective of the breeding program was to develop new compact Carnation cultivars suitable for container production with attractive flower color and early flowering.

The new Carnation originated from a cross made by the Inventor of a proprietary *Dianthus caryophyllus* selection identified as 94602-01 as the female, or seed parent, with a proprietary *Dianthus caryophyllus* selection identified as 87092-02 as the male, or pollen parent. The cultivar 'Kowipa' was discovered and selected by the Inventor as a flowering plant within the progeny of the stated cross in a controlled environment in Aalsmeer, The Netherlands, in 1996.

Asexual reproduction of the new cultivar by terminal cuttings taken at Aalsmeer, The Netherlands, has shown that the unique features of this new Carnation are stable and reproduced true to type in successive generation of asexual reproduction.

SUMMARY OF THE INVENTION

The following traits have been repeatedly observed and are determined to be the unique characteristics of 'Kowipa'. These characteristics in combination distinguish 'Kowipa', as a new and distinct cultivar:

1. Large purple and pink bi-colored flowers.
2. Compact, upright and mounded plant habit.
3. Good basal branching with about 10 lateral branches developing after pinching.
4. Dark green leaves.
5. Rapid growth rate.

6. Fragrant flowers.
7. Good postproduction longevity.

The new Carnation can be compared to the cultivar, 'Sunflor Surprise' (U.S. Plant Pat. application Ser. No. 09/379,263). However, in side-by-side comparisons conducted by the Inventor in Aalsmeer, The Netherlands, plants of the new Carnation differ from plants of the cultivar 'Sunflor Surprise' in the following characteristics:

1. Plants of the new Carnation grow faster and flower earlier than plants of the cultivar 'Sunflor Surprise'.
2. Plants of the new Carnation have larger flowers than plants of the cultivar 'Sunflor Surprise'.
3. Plants of the new Carnation and the cultivar 'Sunflor Surprise' differ in flower color.

A detailed comparison of plants of the cultivar 'Kowipa' and the cultivar 'Sunflor Surprise' appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of typical plants of 'Kowipa'. Flower and foliage colors in the photograph may appear different from the actual colors due to light reflectance.

DETAILED BOTANICAL DESCRIPTION

The cultivar 'Kowipa' has not been observed under all possible environmental conditions. The phenotype may vary somewhat with variations in environment such as temperature and light intensity, without, however, any variance in genotype. The following observations, measurements and comparisons describe plants grown 9-cm pots in Aalsmeer, The Netherlands, under conditions approximating commercial practice in a glass-covered greenhouse with day and night temperatures averaging about 20 and 14° C, respectively. Plants were about 10 weeks old after planting.

In the following description, color references are made to The Royal Horticultural Society Colour Chart except where general terms of ordinary dictionary significance are used.

Botanical classification: *Dianthus caryophyllus* cultivar 'Kowipa'.

Parentage:

*Male parent.*—Proprietary *Dianthus caryophyllus* selection identified as 87092-02.

*Female parent.*—Proprietary *Dianthus caryophyllus* selection identified as 94602-01.

Propagation:

*Type cutting.*—Terminal cuttings.

*Time to initiate roots.*—About 5 days during the summer and about 7 days during the winter.

*Time to develop roots.*—About 20 days during the summer and about 28 days during the winter.

*Root description.*—Fine, freely branching.

Plant description:

*Plant form.*—Compact, upright and mounded; inverted triangle.

*Growth and branching habit.*—Good branching with about ten lateral branches developing after pinching, dense and bushy growth. Appropriate for 9-cm and larger containers.

*Vigor.*—Moderately vigorous.

*Growth rate.*—Rapid growth rate; starting with a plant grown in a 5-cm container, about 10 weeks are required to produce a flowering plant in a 15-cm container.

*Plant height.*—About 9 cm.

*Plant width.*—About 15 cm.

*Lateral branches.*—Diameter: About 3 mm. Internode length: About 7 mm. Color: 138B.

*Foliage description.*—Leaves simple; symmetrical; abundant; opposite & sessile. Quantity of leaves per lateral branch: About 28. Length: About 7 cm. Width: About 5 mm. Shape: Linear; apex, acute; base, cordate; margin, entire. Texture: Smooth, glabrous. Color: Young foliage, upper surface: 138A. Young foliage, lower surface: 138A. Fully expanded foliage, upper surface: 137A. Fully expanded foliage, lower surface: 137B. Venation, upper surface: 137A. Venation, lower surface: 138B.

Flower description:

*Flower type and habit.*—Purple and pink bi-colored double flowers. Freely and continuously flowering. Usually about one or two flowers per lateral branch; typically about 10 open flowers per plant. Flowers flat and convex. Flowers positioned mostly above the foliage; typically facing upright or outward. Flowers persistent.

*Flowering season.*—Year-round under greenhouse conditions. In the garden, flowering is continuous during the summer.

*Flower longevity.*—About two weeks, on the plant.

*Fragrance.*—Strong, clove-like fragrance typical of the species.

*Flower size.*—Diameter: About 3.5 cm. Depth: About 3.5 cm.

*Flower buds.*—Length: About 1.2 cm. Diameter: About 1 cm. Shape: Globular. Color: 138A. Rate of opening: About one week.

*Petals/petaloids.*—Quantity: About 25, overlapping. Length: About 3 cm. Width: About 1.7 cm. Shape: Mostly rounded; apex and base, acute; margin, entire. Texture: Smooth. Color: When opening and fully opened, upper surface: Purple and pink bi-colored; Center splotch 60A, towards base surrounded by and apically, 62B. When opening and fully opened, lower surface: 62B.

*Sepals.*—Quantity: Five. Calyx length: About 2 cm. Calyx width: About 1 cm. Shape: Ovate; apex, rounded; margin, entire. Texture: Smooth. Color: Upper surface: 138C. Lower surface: 139B.

*Peduncles.*—Length: About 2 mm. Angle: Erect. Strength: Strong. Color: 138B.

*Reproductive organs.*—Androecium: Stamen number: Up to five. Anther length: About 2 mm. Anther shape: Oblong. Anther color: 196C. Amount of pollen: Scarce. Gynoecium: Pistil number: Two. Pistil length: About 2.5 cm. Style length: About 2 cm. Style color: 4D. Stigma color: 62B. Ovary color: 144C.

*Seed.*—Size: About 2 by 2 mm. Color: Close to 202A.

Disease resistance: Under commercial conditions, resistance to pathogens common to Dianthus has not been observed.

CHART A

| CHARACTERISTIC | 'KOWIPA' | 'SUNFLOR SURPRISE' |
|---|---|---|
| PLANT HEIGHT | About 9 cm | About 10 cm |
| LATERAL BRANCH DIAMETER | About 3 mm | About 2 mm |
| INTERNODE LENGTH | About 7 mm | About 3 cm |
| QUANTITY OF LEAVES PER LATERAL BRANCH | About 28 | About 6 |
| LEAF LENGTH | About 7 cm | About 8 cm |
| FRAGRANCE | Strong | Moderate |
| FLOWER DIAMETER | About 3.5 cm | About 3 cm |
| FLOWER HEIGHT | About 3.5 cm | About 3 cm |
| PETAL/PETALOID TEXTURE | Smooth | Rippled |
| PETAL/PETALOID MARGIN | Entire | Serrated |
| PETAL/PETALOID LENGTH | About 3 cm | About 2.5 cm |
| PETAL/PETALOID WIDTH | About 1.7 cm | About 1 cm |
| PETAL/PETALOID COLOR, UPPER SURFACE | 60A and 62B | 78A |
| PETAL/PETALOID COLOR, LOWER SURFACE | 62B | 78B |
| SEPAL SHAPE | Ovate | Triangular |
| SEPAL APEX | Rounded | Acute |
| SEPAL COLOR, UPPER SURFACE | 138C | 144B |
| SEPAL COLOR, LOWER SURFACE | 139B | 138A |
| CALYX LENGTH | About 2 cm | About 1.5 cm |
| PEDUNCLE LENGTH | About 2 mm | About 1 mm |

It is claimed:

1. A new and distinct cultivar of Carnation plant named 'Kowipa', as illustrated and described.

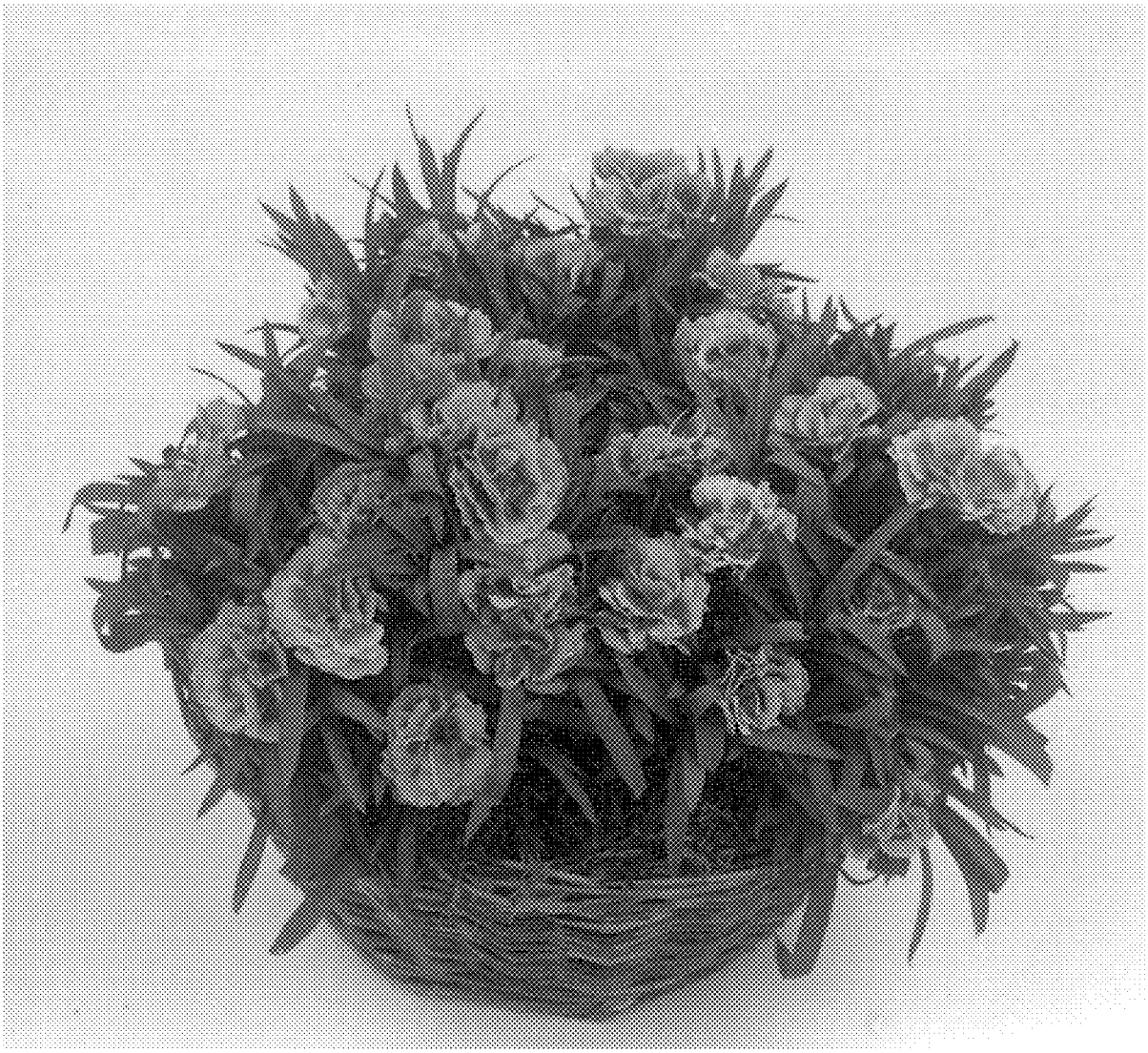

* * * * *